United States Patent
Georgiadis et al.

(10) Patent No.: US 7,908,946 B2
(45) Date of Patent: Mar. 22, 2011

(54) TOOL FOR MACHINING A WORKPIECE MADE OF A HARD MATERIAL

(75) Inventors: Anthimos Georgiadis, Reppenstedt (DE); Michael Kaever, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 667 days.

(21) Appl. No.: 11/795,468

(22) PCT Filed: Jan. 11, 2006

(86) PCT No.: PCT/EP2006/050155
§ 371 (c)(1),
(2), (4) Date: Mar. 24, 2008

(87) PCT Pub. No.: WO2006/077191
PCT Pub. Date: Jul. 27, 2006

(65) Prior Publication Data
US 2008/0196704 A1 Aug. 21, 2008

(30) Foreign Application Priority Data

Jan. 21, 2005 (DE) .......................... 10 2005 003 128
Oct. 11, 2005 (DE) .......................... 10 2005 048 691

(51) Int. Cl.
*B28D 1/18* (2006.01)
*B23C 5/12* (2006.01)
(52) U.S. Cl. ........................................................ 82/1.11
(58) Field of Classification Search ................... 407/53, 407/54, 119, 30; 82/1.11; 428/325, 697; 427/249.7, 249.8
See application file for complete search history.

(56) References Cited

U.S. PATENT DOCUMENTS

| | | | | |
|---|---|---|---|---|
| 2,244,053 | A | * | 6/1941 | Comstock ...................... 428/546 |
| 2,950,523 | A | * | 8/1960 | Frommelt et al. ............. 407/118 |
| 4,909,677 | A | * | 3/1990 | Noguchi et al. ................ 407/66 |
| 5,074,721 | A | * | 12/1991 | Kress et al. .................... 407/119 |
| 6,997,651 | B2 | * | 2/2006 | Kawai et al. .................... 407/53 |
| 7,290,965 | B2 | * | 11/2007 | Gaiser et al. .................. 409/132 |
| 7,758,975 | B2 | * | 7/2010 | Schier .......................... 428/698 |
| 2001/0034007 | A1 | | 10/2001 | Danger et al. |

(Continued)

FOREIGN PATENT DOCUMENTS

BE 903 012 A1 12/1985

(Continued)

OTHER PUBLICATIONS

C. Yalcin, B. K Fussell, Y. Erzan, R. B Jerard: "Real-time calibration of cutting forces model for CNC milling"; Jul. 19-21, 2004; pp. 1-8; [Online] XP007900602 Gefunden im Internet: URL: http://www.unh.edu/dml/publications/2004/UL_030_2004.pdf; Proceedings of 2004 JUSFA—2004 Japan—USA Symposium on Flexible Automation; Denver, Colorado.

*Primary Examiner* — Will Fridie, Jr.

(57) ABSTRACT

There is described a tool as well as a method for machining a workpiece made of a hard material by means of a geometrically determined blade. In order to obtain an improved surface quality of the machined workpiece when machining such a hard and brittle material, a tool is provided which has a cutting angle of less than 10°. According to the associated machining method, rotational speeds exceeding 1300 rpm are used. There is further described a machine that is to be used in such a tool and is utilized in such a method.

18 Claims, 3 Drawing Sheets

U.S. PATENT DOCUMENTS

2004/0170480 A1  9/2004  Kawai et al.

FOREIGN PATENT DOCUMENTS

| DE | 42 36 823 A1 | 2/1994 |
| DE | 199 01 176 A1 | 7/2000 |
| DE | 199 01 929 A1 | 7/2000 |
| DE | 199 06 858 A1 | 8/2000 |
| DE | 100 24 129 C1 | 10/2001 |
| DE | 203 14 717 U1 | 2/2004 |
| EP | 0 922 551 A2 | 6/1999 |
| EP | 1 004 414 A | 5/2000 |
| EP | 1 201 776 A2 | 5/2002 |

\* cited by examiner

TOOL FOR MACHINING A WORKPIECE MADE OF A HARD MATERIAL

CROSS REFERENCE TO RELATED APPLICATIONS

This application is the US National Stage of International Application No. PCT/EP2006/050155, filed Jan. 11, 2006 and claims the benefit thereof. The International Application claims the benefits of German application No. 10 2005 003 128.5 DE filed Jan. 21, 2005 and German application No. 10 2005 048 691.6 DE filed Oct. 11, 2005, all of the applications are incorporated by reference herein in their entirety.

FIELD OF INVENTION

The invention relates to a tool for machining a workpiece made of a hard material by means of a geometrically determined blade of the type specified in the preamble of claim 1. The invention also relates to a machine for machining such a workpiece according to the preamble of claim 10.

BACKGROUND OF INVENTION

Hard materials at hand are for example materials such as granite, marble, concrete, asphalt, brickwork, ceramics, mixed ceramics, or ceramic glasses. Generally, hard materials at hand are materials which promote the abrasion—that is the abrasion of tools—to a considerable extent. Due to the abrasive properties, these materials are therefore often machined by means of geometrically undetermined blades—for example by grinding.

From DE 100 24 129 C1 and from EP 0 922 551 A2 are already known methods for machining rock where a material removal takes place by means of geometrically determined blades in the form of a milling process. With these known methods, an impact mechanism is used respectively, where a radial impact frequency is induced by an integrated pendulum or wobble tube. These methods can however only be used when a coarse surface of the machined surface can be accepted.

In particular, considerably higher demands are made of the surface quality when machining ceramics, mixed ceramics or ceramic glass, which up to now are only achieved by the known methods by means of a geometrically undetermined blade such as grinding. These machining methods are often implemented using a coolant and/or a lubricant. The fact that residues of these operating fluids often remain near the surface within the hard material is disadvantageous. This can lead to allergic reactions in the patient, for example, in the medical or dental sector.

In US 2004/170480 A1 is disclosed a tool for machining a material that is difficult to remove, for example, a heat-resistant alloy or stainless steel where the blade is geometrically determined and comprises a blade angle of less than 10°.

The article by C. Yalcin, B. K Fussell, Y. Erzan and E. B. Jerard: "Real-time calibration of cutting forces model for CNC milling", found on the internet under the URL: http://www.unh.edu/dml/publications/2004/UL_030_2004.pdf, Proceedings of 2004 JUSFA—2004 Japan—USA Symposium on Flexible Automation, Denver, Colo., Jul. 19-21, 2004 describes a detailed model for cutting forces with CNC machines.

SUMMARY OF INVENTION

An object of the present invention is thus to create a tool and a method of the above-mentioned type, with which an improved surface quality can be achieved with workpieces of a hard material. Furthermore, a machine for use with such a tool and for carrying out such a method shall be created.

The object is achieved according to the invention by a tool and a method with features of independent claims. Furthermore, the solution according to the invention results also from a machine. Advantageous embodiments with practical and non-trivial further developments of the invention are given in the further dependent claims.

With the tool according to the invention, the cutting angle of the blade is formed smaller than 10°, and preferably comprises an angular dimension between 4° and 6°. The cutting angle is thereby determined by the contact width of the tool and projects from the cutting point—that is the entry of the blade into the workpiece—to the exit point of the blade from the workpiece. Such a flat cutting angle has proved to be ideal to achieve very small cutting forces and surfaces with a machining accuracy of 2 µm and an average roughness depth of $\leq 0.2$ µm. The relatively small cutting forces that occur because of the small cutting angle thus favor an extremely long holding time of the tool. Due to the very flat cutting angle, the blade acts in a similar way to a chisel, which does not remove chips during machining unlike metals, but which rather effects a continual material breakage.

According to the invention, a crystalline coating like e.g. a diamond coating of the tool at least in the region of the blade is provided whereby a layer thickness of 15 µm to 30 µm has been proved to be particularly stable. The extremely small grain size of about 20 nm to about 100 nm of the diamond coating leads to a particularly small surface roughness of the workpiece.

The tool geometry according to the invention has been shown to be particularly advantageous with the so-called HSC milling (high speed cutting), where in particular 5 to 10 times higher cutting speeds and feeds are used than with conventional machining. The term HSC milling is presently also used with some smaller rotational speeds in the transition region to conventional milling, as this machining method is basically not determined by the rotational speed of the spindle or the rotational speed of the tool alone, but also by other dimensions and method parameters as for example the machining cross section and the feed. In other words, in connection with hard and brittle materials, one already speaks of HSC milling with about 1300 rotations per minute. Very fine structures can thus be facilitated even with tool diameters smaller than 1 mm with very high cutting speeds and very high rotational speeds, whereby the freedom and the flexibility in the surface and the workpiece design can be increased considerably and the manufacturing time can be reduced accordingly. A further advantage relates in particular to a connection with ceramics in that materials can also be machined in the annealed state and that the shrinkage process does not have to be considered anymore. The temperature of the blade only increases slightly in spite of the increased cutting or feed speed, as the feed speed exceeds the heat conduction speed of the workpiece and the tool thereby leads in front of the heat dispersion within the hard material. The relatively low cutting forces also effect a low and continually constant tool displacement. Spindle bearings, guideways and further devices of the machining apparatus are accordingly preserved.

In contrast to the usual machining methods, where tools with an angle of twist of about 20° are used, it has been shown to be particularly advantageous with the new machining method with the tool according to the invention to use a far larger angle of twist larger than 35° and preferably between 40° and 41°. Such a large angle of twist enables lower cutting forces, particularly smooth surfaces of the workpiece and longer holding times of the tool in connection with the very flat cutting angle.

With the equation according to claim 4, parameters and geometric data of the tool such as cutting angle, angle of twist, layer thickness of a diamond coating, diameter, tooth number or the like can be determined particularly accurately by means of the specific cutting force components, as no chip removal takes place with hard and brittle materials, but rather a material breakage. While a linear and direction-independent cutting force is assumed with the continual chip formation, a division of the cutting force in direction-dependent components is necessary with hard and brittle materials, which are preferably given in a Cartesian coordinate system. Likewise it is also feasible to choose other coordinate systems.

A particularly smooth surface can be achieved by a small cutting width of the tool, which is in a range of 0.01 mm to 0.2 mm and preferably 0.02 mm with the apparatus according to the invention. Furthermore, a very good surface quality can be achieved by a cutting depth of the tool in a region of 0.5 mm to 4 mm, and in particular 2 mm. A cutting speed in the region of 50 to 150 m/min ensures that the heat conduction speed of the machined base material is exceeded and that the tool leads in front of the heat dispersion within the workpiece.

BRIEF DESCRIPTION OF THE DRAWINGS

Further advantages, characteristics and details of the invention result from the following description of the tool and the associated machining method and by means of the drawings and diagrams; these show.

DETAILED DESCRIPTION OF INVENTION

Figure 1:
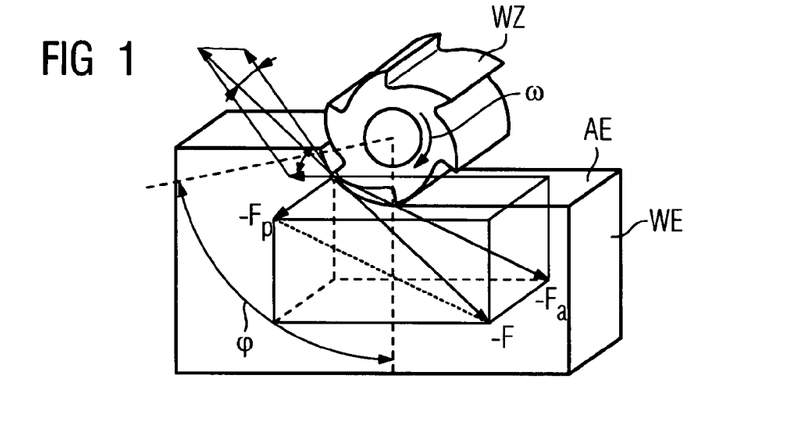
FIG. 1 a schematic perspective of a tool engaging a workpiece, whereby components of the cutting force and associated angles are shown in particular.

In FIG. 1, a tool WZ engaging a workpiece WE is shown in schematic perspective in the form of a peripheral milling cutter which is operated in counter rotation with the angle speed $\omega$. A machining force or cutting force F is divided into an active force $F_a$ and a passive force $F_p$ based on a working plane AE. The active force $F_a$ in the working plane AE is thereby power-determining for the chip formation. The passive force $F_p$ vertical to the working plane AE is however not involved during the machining.

The active force $F_a$ is divided into a cutting force $F_c$ based on the cutting direction, into a feed force $F_f$ based on the feed direction:

$$F = \sqrt{F_a^2 + F_p^2} = \sqrt{F_c^2 + F_f^2 + F_p^2}. \tag{1}$$

A cutting angle $\phi$ is determined by the contact width ae of the tool WZ and projects from the cutting point—that is the entry of the blade of the tool WZ into the workpiece WE—to the exit point of the blade from the workpiece WE.

The cutting force law by Kienzle has dominated as the method of calculation for the performance-guided cutting force $F_c$. The specific cutting force $k_c$ is thereby the ratio of the cutting force $F_c$ to the machining cross section A. This machining cross section occurring during a machined withdrawal results as a function of a machining width b and a machining thickness h:

$$k_c = \frac{F_c}{A} = \frac{F_c}{a_p \cdot f} = \frac{F_c}{b \cdot h}. \tag{2}$$

The specific cutting force $k_c$ is the part of the cutting force $F_c$ which acts on 1 mm² of the machining cross section A. However, $k_c$ is not constant, but is influenced by different factors. The specific cutting force $k_c$ is a material-dependent machining value which hardly depends on the machining width b, but nearly exclusively on the machining thickness h or t and a feed f. If the chip removal is larger, the necessary specific cutting force $k_c$ will become smaller. The machining thickness h or t changes hereby during the milling. One proceeds then from a mean machining thickness $h_m$ for determining the cutting force $F_c$. When the insertion depth increases thereby, the removing width decreases. The value of the specific cutting force $k_c$ sinks thereby. Kienzle was the first to express this relation by a power law:

$$k_c = k_{c1.1} \cdot h^{-Z_c} \text{ in N/mm}^2. \tag{3}$$

The specific cutting force $k_{c1.1}$ indicates the cutting force $k_c$ based on a machining width b of 1 mm and a machining thickness h of 1 mm. This dependence is generally represented as a straight line in the double-logarithmic scale. An exponent $Z_c$ represents the gradient of the straight line $k_c = f(h)$ in this coordinate system.

If the equation (3) is introduced into the cutting force formula (2) by Kienzle, the following results:

$$F_c = b \cdot h^{1-Z_c} \cdot k_{c1.1}. \tag{4}$$

The exponent $1-Z_c$ describes here the increase value of the specific cutting force $k_{c1.1}$. The Kienzle machining force model valid up to now can only be used in a limited manner for the machining of hard and brittle materials, which is particularly due to the erratic material breakage during the machining. This known approach was expanded as follows:

According to Martelotti, the following is valid for the current differential cutting force $dF_{cutting}$ for a tooth or a blade:

$$d\vec{F}_{cutting} = \vec{K}_{cutting} t db, \tag{5}$$

with a (specific) machining thickness t and a differential db of the cutting depth or the machining width b.

Figure 4:
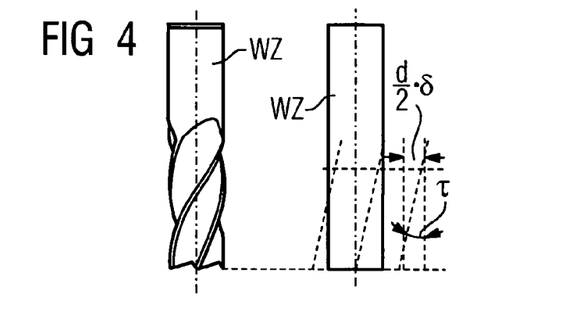
FIG. 4 a schematic side view of an end milling cutter.

The cutting force dF is thereby the sum of two cutting forces—namely a cutting force cutting the material $dF_{cutting}$ and a deformation force $dF_{edge}$ on the blade. It is assumed here that the angle of twist ($\lambda$) (FIG. 4) of the tool WZ is zero:

$$d\vec{F} = d\vec{F}_{edge} + d\vec{F}_{cutting}, \tag{6a}$$

$$d\vec{F} = \vec{K}_{edge} db + \vec{K}_{cutting} t db, \tag{6b}$$

with a specific force $K_{edge}$ on the blade and a specific cutting force $K_{cutting}$.

Figure 2:
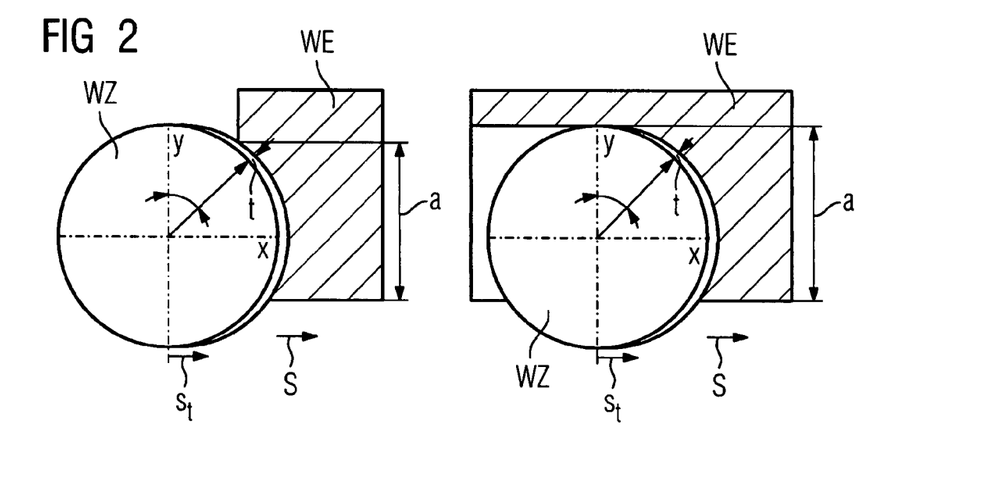
FIG. 2 respectively a schematic cross sectional view through a tool during the insertion into a workpiece and in the completely inserted position for the explanation of the torques occurring thereby.

FIG. 2 shows the tool WZ being inserted into a workpiece WE or the torques resulting thereby during the machining in a schematic cross-section. The tool WZ is shown on the left at the beginning of the insertion into the workpiece WE, whereby a cutting width a of the tool WZ changes depending on the feed S per tooth $s_t$ and the mean cutting force thus increases with time. The cutting width a on the right is constant and the cutting force is periodic. The (specific) machining thickness t for every point of the blade can be calculated as a function of the angular position $\Phi$ of the point and the feed per tooth $s_t$:

$$t = s_t \sin\phi, \tag{7}$$

with a current insertion angle $\Phi$ which determines the position on the blade point when it is in contact with the workpiece WE. The feed $s_t$ per tooth results from:

$$s_t = \frac{v}{\omega N_f}, \tag{8}$$

with a speed v, the angular speed $\omega$ and a tooth number $N_f$ of the milling cutter.

The differential db of the cutting depth can be determined as follows according to FIG. 3, where the tool WZ which is inserted into the workpiece WE can be seen in a schematic plan view or in a side view:

$$db = \frac{d}{2\tan\lambda} d\phi, \tag{9}$$

with a milling cutter diameter d, and angle of twist $\lambda$ and the insertion angle $\Phi$. Accordingly, the point on the blade delays behind the associated end point of the blade by the angle of twist $\lambda$. The delay angle $\delta$ thereby results from:

$$\delta = \frac{2b\tan\lambda}{d}, \tag{10}$$

with the cutting depth or the machining width b and the milling cutter diameter d.

Figure 3:
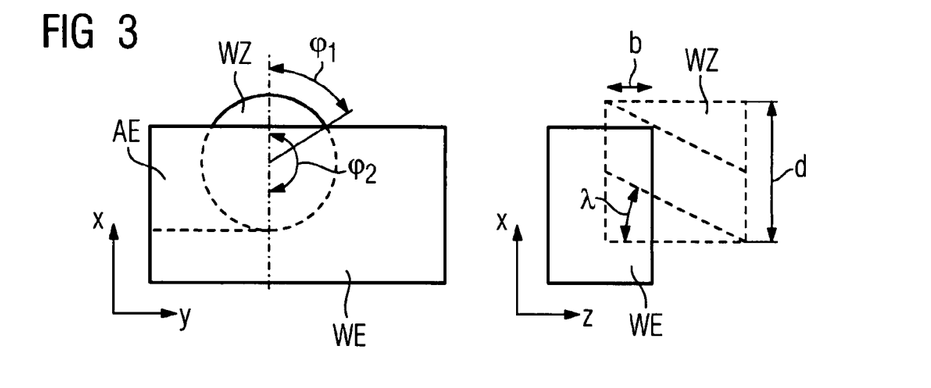
FIG. 3 a schematic cross sectional view and a schematic side view of a tool being inserted into a workpiece, by means of which the present milling geometry is explained.

The delay angle $\delta$ can be seen in combination with FIG. 4, where a tool WZ formed as an end milling cutter is shown in a schematic side view. The delay angle $\delta$ is thereby used to classify the cutting geometry as type 1 or type 2:

$$\text{Type I} \rightarrow \delta \leq \phi_2 - \phi_1$$

$$\text{Type II} \rightarrow \delta > \phi_2 - \phi_1, \tag{11}$$

with an entry and exit angle $\phi_1$ and $\phi_2$ (FIG. 3). Type 1 is used when the entire blade contacts the workpiece WE for a certain time; type 2 is used when the entire blade contacts the workpiece WE only for a moment, or when any parts of the blade do not have any contact at all with the workpiece WE. The cutting force F according to equation (6b) results as:

$$\vec{F} = \int \vec{K}_{edge} db + \int \vec{K}_{cutting} t db \tag{12}$$

$$= \int (\vec{K}_{edge} + \vec{K}_{cutting} s_t \sin\phi) \frac{d}{2\tan\lambda} d\phi.$$

The following cutting force $F_c$ based on the tooth number $N_f$ of the milling cutter results thereby:

$$\vec{F} = \sum_{i=1}^{N_f} \vec{F}_i. \tag{13}$$

In this formula, all cutting forces $F_i$ are calculated at one point of time, as all differential parts of the cutting force $F_c$ are calculated for every cut. The change of the cutting force vector ((F(t)) is expressed as the multiplication of the functions in the time:

$$\vec{F}(t) = \vec{K}_{edge}(t) h(t) + \vec{K}_{cutting}(t) A(t). \tag{14}$$

The specific cutting forces $K_{edge}(t)$ and $K_{cutting}(t)$ are multiplied with the scalar function or the contact length h(t) of the blade with the workpiece WE and the machining cross section A (t). The time variable can be replaced by the insertion angle $\theta$ of the fixed point on the peripheral milling cutter and by the angular speed $\omega$ of the tool WE:

$$\vec{F}(t) = \vec{F}\left(\frac{\theta}{\omega}\right) = \vec{F}(\theta), \tag{15a}$$

$$\vec{F}(\theta) = \vec{K}_{edge}(\theta) h(\theta) + \vec{K}_{cutting}(\theta) A(\theta). \tag{15b}$$

The functions h(t) and A(t) will be calculated separately in the following.

Figure 5:
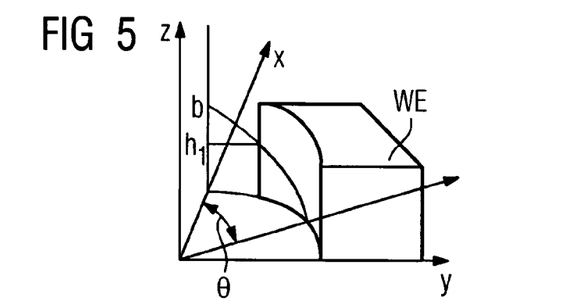
FIG. 5 a schematic perspective of the engagement of a blade of the tool in the workpiece and associated geometric data.

FIG. 5 shows the contact length $h_1$ of the first blade in the gradient of the insertion angle $\theta$ in the Cartesian coordinate system. The following equation results for the contact length $h_1(\theta)$:

$$h_1(\theta) = \int_{L_1(\theta)}^{L_2(\theta)} \frac{d}{2\tan\lambda} d\theta, \tag{16}$$

with the milling cutter d, the angle of twist $\lambda$, the insertion angle $\theta$ and $L_1$ nd $L_2$ as functions of the insertion angle $\theta$. These two values $L_1$, $L_2$ are, as can be seen in the following tables, calculated for every milling phase of the insertion angle $\theta$. Every blade passes through three phases according to the following table from the entry angle $\phi_1$ to the exit angle $\phi_2$:

Phase A, in which the tool WZ engages in the workpiece WE and every rotation $d\phi$ enlarges the contact length h of the blade with the workpiece WE. Phase B, where the contact length h of the blade with the workpiece WE is constant. Phase C, where the contact length h reduces.

|  | Type 1 | | Type 2 | |
|---|---|---|---|---|
| Phase | $L_1(\theta)$ | $L_2(\theta)$ | $L_1(\theta)$ | $L_2(\theta)$ |
| Für $e_1 < \theta \leq e_2$ - Phase A | $\phi_1$ | $\theta$ | $\phi_1$ | $\theta$ |
| Für $e_2 < \theta \leq e_3$ - Phase B | $\theta - \delta$ | $\theta$ | $\theta - \delta$ | $\theta$ |
| Für $e_3 < \theta \leq e_4$ - Phase C | $\theta - \delta$ | $\phi_2$ | $\theta - \delta$ | $\phi_2$ |

The values of $e_1$, $e_2$ and $e_3$ can be taken from the following table.

|  | Type 1 | Type 2 |
|---|---|---|
| $e_1$ | $\phi_1$ | $\phi_1$ |
| $e_2$ | $\phi_1 + \delta$ | $\phi_2$ |
| $e_3$ | $\phi_2$ | $\phi_1 + \delta$ |

Figure 6:
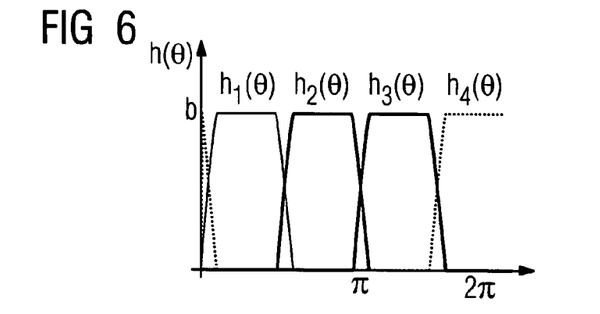
FIG. 6 a diagram of the contact length of each blade of the tool during the course of the rotation.

For the arbitrary blade the following contact length $h_n$ is obtained according to equation (16):

$$h_n(\theta) = \int_{L_1(\theta + \xi(n-1))}^{L_2(\theta + \xi(n-1))} \frac{d}{2\tan\lambda} d\theta, \tag{17}$$

with the milling cutter diameter d, the angle of twist $\lambda$, the insertion angle $\theta$, an angle $\xi$ between the blades, the number n of the blade and $L_1$ and $L_2$ as functions not only of the insertion angle $\theta$, but also the number n of the blade. The angle $\xi$ between the blades is thereby:

$$\xi = \frac{2\pi}{N_f}, \tag{18}$$

with the tooth number $N_f$ of the milling cutter. For the entire contact length results:

$$h(\theta) = \sum_{n=1}^{N_f} h_n(\theta), \tag{19}$$

with the insertion angle $\theta$, the number n of the blade and the contact length $h_n$ of the nth blade with the workpiece WE. The contact length $h_{(\theta)}$ of each blade for a milling cutter with 4 teeth is shown in FIG. 6.

Figure 7:
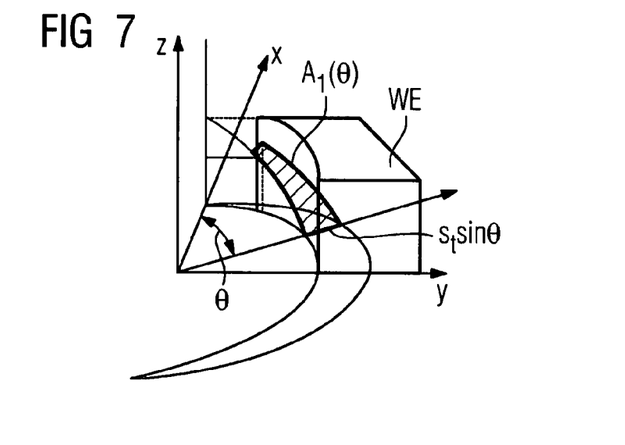
FIG. 7 a schematic perspective of the machining cross section produced by the blade during the engagement into the workpiece.

In FIG. 7 is shown the machining cross section $A_n$ of the first blade with an insertion angle $\theta$ in the workpiece WE in perspective. The entry angle $\phi_1$ and the exit angle $\phi_2$ are thus 30° or π/2. For the machining cross section $A_1$ results:

$$A_1(\theta) = \int_{L_1(\theta)}^{L_2(\theta)} \frac{s_t d}{2\tan\lambda} \sin\theta d\theta, \tag{20}$$

with the feed $s_t$ per tooth, the milling cutter diameter d, the angle of twist $\lambda$, the insertion angle $\theta$ and $L_1$ and $L_2$ as functions of the insertion angle $\theta$. These two values $L_1$, $L_2$ have to be calculated for every milling phase of the insertion angle $\theta$.

Figure 8:
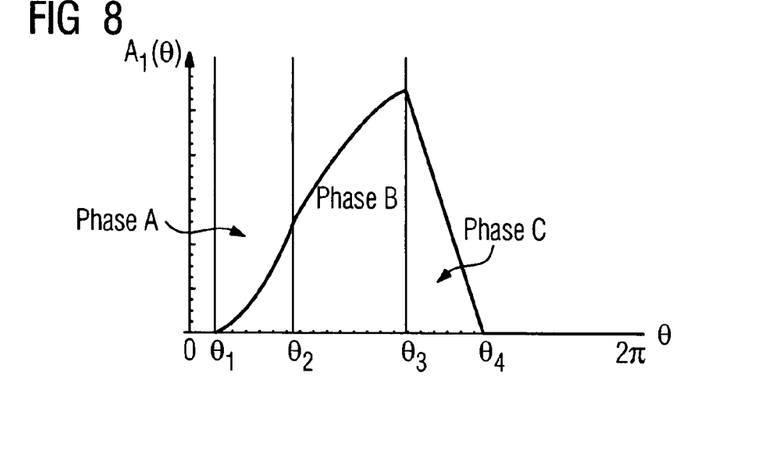
FIG. 8 a diagram of the chronological course of the machining cross section for a blade and a cutting geometry during a tool rotation.

The machining cross section $A_1$ for a blade n and a cutting geometry of type 1 is shown in FIG. 8 for the three phases A, B, C according to the above table. The machining cross section $A_n$ can be determined for any arbitrary blade n according to the following equation:

$$A_n(\theta) = \int_{L_1(\theta + \xi(n-1))}^{L_2(\theta + \xi(n-1))} \frac{s_t d}{2\tan\lambda} \theta d\theta, \tag{21}$$

with the feed $s_t$ per tooth, the milling cutter diameter d, the angle of twist $\lambda$, the insertion angle $\theta$, the angle $\xi$ between the blades, the number n of the blade and $L_1$ and $L_2$ as functions of $\theta$ and n. As the final machining cross section results:

$$A(\theta) = \sum_{n=1}^{N_f} A_n(\theta), \tag{22}$$

with the tooth number $N_f$ of the milling cutter, the insertion angle $\theta$, the number n of the blade and the machining cross section $A_n$ at the nth blade.

Figure 9:
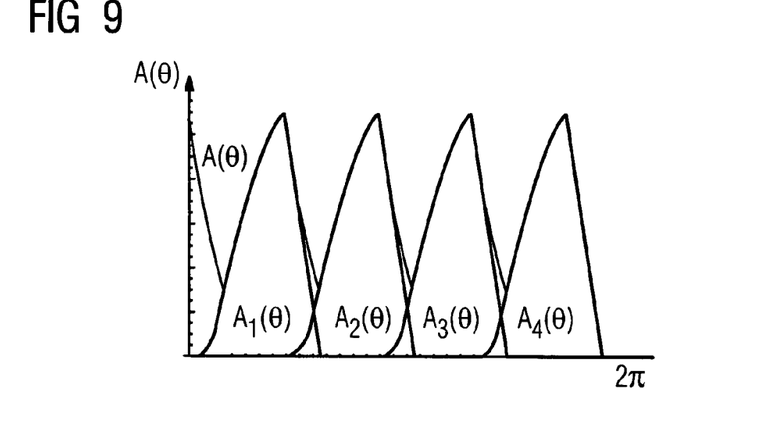
FIG. 9 a diagram of the machining cross section for four blades of a milling cutter during the course of the tool rotation; and in FIG. 10 a diagram of the course of the specific components of the cutting force during the rotation of the tool.

In FIG. 9 is accordingly shown the machining cross section $A(\theta)$ for a milling cutter with 4 blades (angle $\xi$ between the blades=90°). So as to compare the obtained data with experimental data, the cutting force has to be divided based on the x-, y-, z-directions into $F_x$, $F_y$ and $F_z$:

$$\vec{F}(\theta) = \begin{bmatrix} F_x(\theta) \\ F_y(\theta) \\ F_z(\theta) \end{bmatrix} \tag{23}$$

$$= A(\theta)\begin{bmatrix} K_{cx}(\theta) \\ K_{cy}(\theta) \\ K_{cz}(\theta) \end{bmatrix} + h(\theta)\begin{bmatrix} K_{ex}(\theta) \\ K_{ey}(\theta) \\ K_{ez}(\theta) \end{bmatrix},$$

with the machining cross section A, the contact length h of the blade with the workpiece WE, the insertion angle $\theta$, the components of the specific cutting force $K_{cx}$, $K_{cy}$, $K_{cz}$ and the components of the specific cutting force $K_{ex}$, $K_{ey}$, $K_{ez}$ on the blade.

The specific cutting force is not to be divided in x-, y-, z-directions, but in t-, r-, z-directions tangentially, radially and axially consistent with the tool. The new functions $A_R(\theta)$ and $h_R(\theta)$ are used for this:

$$\begin{bmatrix} F_x(\theta) \\ F_y(\theta) \\ F_z(\theta) \end{bmatrix} = A_R(\theta)\begin{bmatrix} K_{cx}(\theta) \\ K_{cy}(\theta) \\ K_{cz}(\theta) \end{bmatrix} + h_R(\theta)\begin{bmatrix} K_{ex}(\theta) \\ K_{ey}(\theta) \\ K_{ez}(\theta) \end{bmatrix}. \tag{24}$$

The functions $A_R(\theta)$ and $h_R(\theta)$ are indeed the product of the rotary matrix $R(\theta)$ or of the machining cross section A and the contact length h:

$$R(\theta) = \begin{pmatrix} \cos(\theta) & \sin(\theta) & 0 \\ \sin(\theta) & -\cos(\theta) & 0 \\ 0 & 0 & 1 \end{pmatrix}, \tag{25}$$

with the insertion angle $\theta$.

As rotary matrix $R_n(\theta)$ for every blade is obtained:

$$R_n(\theta) = \begin{pmatrix} \cos(\theta + \xi(n-1)) & \sin(\theta + \xi(n-1)) & 0 \\ \sin(\theta + \xi(n-1)) & -\cos(\theta + \xi(n-1)) & 0 \\ 0 & 0 & 1 \end{pmatrix}, \quad (26)$$

with the insertion angle $\theta$, the angle $\xi$ between the blades and the number n of the blades.

For all blades for the rotated machining cross section $A_R$ the following is valid:

$$A_R(\theta) = \sum_{n=1}^{N_f} R_n(\theta) A_n(\theta), \quad (27)$$

with the rotary matrix $R_n$ for the nth blade, the machining cross section $A_n$ at the nth blade, the insertion angle $\theta$, the tooth number $N_f$ of the milling cutter and the number n of the blade.

The rotated contact length $h_R$ is calculated from:

$$h_R(\theta) = \sum_{n=1}^{N_f} R_n(\theta) h_n(\theta), \quad (28)$$

with the rotary matrix $R_n$ for the nth blade, the contact length $h_n$ of the nth blade, the insertion angle $\theta$, the tooth number $N_f$ of the milling cutter and the number n of the blade.

So as to simplify the calculations, $S_1(\theta)$, $S_2(\theta)$, $S_3(\theta)$ und $S_4(\theta)$ are defined:

$$S_1(\theta) = \sum_{n=1}^{N_f} A_n(\theta) \cos(\theta + \xi(n-1)), \quad (29a)$$

$$S_2(\theta) = \sum_{n=1}^{N_f} A_n(\theta) \sin(\theta + \xi(n-1)), \quad (29b)$$

$$S_3(\theta) = \sum_{n=1}^{N_f} h_n(\theta) \cos(\theta + \xi(n-1)), \quad (29c)$$

$$S_4(\theta) = \sum_{n=1}^{N_f} h_n(\theta) \sin(\theta + \xi(n-1)), \quad (29d)$$

with the machining cross section $A_n$ at the nth blade, the contact length $h_n$ of the nth blade, the insertion angle $\theta$, the tooth number $N_f$ of the milling cutter, the number n of the blade and the angle $\xi$ between the blades.

If the equations (29a-d) are introduced into equation (24), the following results:

$$\begin{bmatrix} F_x(\theta) \\ F_y(\theta) \\ F_z(\theta) \end{bmatrix} = \begin{bmatrix} S_1(\theta) & S_2(\theta) & 0 & S_3(\theta) & S_4(\theta) & 0 \\ S_2(\theta) & -S_1(\theta) & 0 & S_4(\theta) & -S_3(\theta) & 0 \\ 0 & 0 & A(\theta) & 0 & 0 & h(\theta) \end{bmatrix} \begin{bmatrix} K_{ct}(\theta) \\ K_{cr}(\theta) \\ K_{cz}(\theta) \\ K_{et}(\theta) \\ K_{er}(\theta) \\ K_{ez}(\theta) \end{bmatrix}. \quad (30)$$

If the second matrix in equation (30) is described as letter J, the following results:

$$J(\theta) = \begin{bmatrix} S_1(\theta) & S_2(\theta) & 0 & S_3(\theta) & S_4(\theta) & 0 \\ S_2(\theta) & -S_1(\theta) & 0 & S_4(\theta) & -S_3(\theta) & 0 \\ 0 & 0 & A(\theta) & 0 & 0 & h(\theta) \end{bmatrix}. \quad (31)$$

For every $\theta$ the following relation is valid:

$$K(\theta) = J^{-1}(\theta) F(\theta). \quad (32)$$

During the calculation of equation (32) results the problem that three parameters and six unknown variables are present. To solve this problem, it is assumed that two successive points have the same specific cutting forces. The specific cutting forces for every interval are calculated as such:

$$\begin{bmatrix} F_x(\theta) \\ F_y(\theta) \\ F_z(\theta) \\ F_x(\theta + d\theta) \\ F_y(\theta + d\theta) \\ F_z(\theta + d\theta) \end{bmatrix} = J_A(\theta) \begin{bmatrix} K_{ct}(\theta) \\ K_{cr}(\theta) \\ K_{cz}(\theta) \\ K_{et}(\theta) \\ K_{er}(\theta) \\ K_{ez}(\theta) \end{bmatrix}. \quad (33)$$

The matrix J has to be supplemented by the square matrix.

$$J_A(\theta) = \begin{bmatrix} S_1(\theta) & S_2(\theta) & 0 & S_3(\theta) & S_4(\theta) & 0 \\ S_2(\theta) & -S_1(\theta) & 0 & S_4(\theta) & -S_3(\theta) & 0 \\ 0 & 0 & A(\theta) & 0 & 0 & h(\theta) \\ S_1(\theta + d\theta) & S_2(\theta + d\theta) & 0 & S_3(\theta + d\theta) & S_4(\theta + d\theta) & 0 \\ S_2(\theta + d\theta) & -S_1(\theta + d\theta) & 0 & S_4(\theta + d\theta) & -S_3(\theta + d\theta) & 0 \\ 0 & 0 & A(\theta + d\theta) & 0 & 0 & h(\theta + d\theta) \end{bmatrix}. \quad (34)$$

It results as specific cutting forces:

$$\begin{bmatrix} K_{ct}(\theta) \\ K_{cr}(\theta) \\ K_{cz}(\theta) \\ K_{et}(\theta) \\ K_{er}(\theta) \\ K_{ez}(\theta) \end{bmatrix} = [J_A(\theta)]^{-1} \begin{bmatrix} F_x(\theta) \\ F_y(\theta) \\ F_z(\theta) \\ F_x(\theta+d\theta) \\ F_y(\theta+d\theta) \\ F_z(\theta+d\theta) \end{bmatrix}. \quad (35)$$

After the mean specific cutting forces have been determined, the semi-empirical cutting forces $F_x$, $F_y$, $F_z$ can be calculated with their help and can be compared to experimental data if necessary:

$$\begin{bmatrix} F_x(\theta) \\ F_y(\theta) \\ F_z(\theta) \end{bmatrix} = J(\theta) \begin{bmatrix} \overline{K}_{ct}(\theta) \\ \overline{K}_{cr}(\theta) \\ \overline{K}_{cz}(\theta) \\ \overline{K}_{et}(\theta) \\ \overline{K}_{er}(\theta) \\ \overline{K}_{ez}(\theta) \end{bmatrix}, \quad (36)$$

with the mean specific cutting forces $\overline{K}_{ct}, \overline{K}_{cr}, \overline{K}_{cz}, \overline{K}_{et}, \overline{K}_{er}, \overline{K}_{ez}$.

Figure 10:
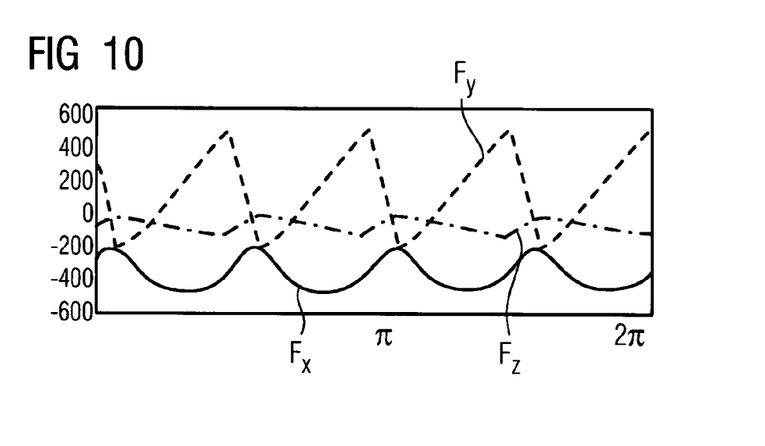

By means of the process modeling established above (FIG. 10), the course of the specific cutting force components of a 4-cutting milling head is shown in the course of the rotation. According to the above mechanistic model, the tangential cutting force $F_t(\phi)$, the radial cutting force $F_r(\phi)$, and the axial cutting force $F_a(\phi)$ are determined as a function of the changing machining cross section $ah(\phi)$ and the cutting depth a:

$$F_t(\phi) = K_{tc}ah(\phi) + K_{te}a,$$

$$F_r(\phi) = K_{rc}ah(\phi) + K_{re}a,$$

$$F_a(\phi) = K_{ac}ah(\phi) + K_{ae}a,$$

with the force coefficients or specific cutting forces $K_{tc}$, $K_{rc}$, $K_{ac}$, by the shear or machining process in the tangential, radial and axial direction, and with the specific cutting forces $K_{te}$, $K_{re}$, $K_{ae}$, which indicate the material removal at the edge of the blade.

Due to the process modeling shown above, a tool WZ was determined, whose blades comprise a cutting angle φ smaller than 10° and in particular between 4° to 6° and accordingly perform a chiseling effect on the hard material, so that a very controlled material breakage can be produced. The tool WZ comprises, at least in the region of the blades a crystalline diamond coating and in particular a so-called nanocrystalline multi or double layer with a layer thickness of 23 μm plus 3 μm and a grain size of 20 nm to 100 nm. Their layer thickness varies between 15 nm and 30 nm. The tool WZ designed as a milling cutter preferably has an angle of twist δ larger than 35°, and particularly from 40° to 41°. For the machining of ceramics, the tool WZ is operated as a milling cutter with a cutting width ae from 0.01 mm to 0.2 mm, and in particular with a cutting width ae of 0.02 mm. Furthermore, the tool WZ is constructed in such a manner that a cutting depth ap of 0.5 mm to 4 mm and in particular 2 mm can be realized. Furthermore, the tool WZ is constructed in such a manner that it can be operated with a cutting speed of 50 to 150 m/min. It is obvious that the diameter d of a tool WZ formed as an end milling cutter or a radius miller can vary within a large range; with the machining of ceramics however, a diameter d of about 6 mm has proved to be particularly suitable. With a tool WZ formed as a radius cutter, a corner radius of 0.2 mm to 0.6 mm is preferably provided thereby.

With regard to the machining method and the machining type, a feed $s_t$ per tooth in the magnitude of 0.06 mm and a rotational speed between 2650 rpm to 7800 rpm have proved to be particularly suitable as parameters in addition to the above described cutting speed V.

The invention claimed is:

1. A tool for machining a workpiece, comprising:
   a blade with a blade having a cutting angle smaller than 10°; and
   a crystalline diamond coating provided at least in the region of the blade, wherein the tool is characterized by parameters determined as a function of specific cutting force components by means of the equation $$\begin{bmatrix} F_x(\theta) \\ F_y(\theta) \\ F_z(\theta) \end{bmatrix} = J(\theta) \begin{bmatrix} \overline{K}_{ct}(\theta) \\ \overline{K}_{cr}(\theta) \\ \overline{K}_{cz}(\theta) \\ \overline{K}_{et}(\theta) \\ \overline{K}_{er}(\theta) \\ \overline{K}_{ez}(\theta) \end{bmatrix}$$

whereby $\overline{K}_{ct}, \overline{K}_{cr}, \overline{K}_{cz}, \overline{K}_{et}, \overline{K}_{er}, \overline{K}_{ez}$ are mean specific cutting forces.

2. The tool as claimed in claim 1, wherein the cutting angle smaller is in a range between 4° and 6°, and wherein the tool is to be used for machining the workpiece out of a hard material.

3. The tool as claimed in claim 1, wherein an angle of twist is larger than 35°.

4. The tool as claimed in claim 1, wherein the angle of twist is in a range between 40° and 41°.

5. The tool as claimed in claim 1, wherein the crystalline diamond coating comprises a grain size of 20 nm to 100 nm and a layer thickness of 15 nm to 30 nm.

6. The tool as claimed in claim 1, wherein the tool is selected from the group consisting of a face cutter, an end milling cutter, a pin miller and a radius miller.

7. The tool as claimed in claim 1, wherein a cutting width is in a range from 0.01 mm to 0.2 mm.

8. The tool as claimed in claim 1, wherein a cutting depth is in a range from 0.5 mm to 4 mm.

9. The tool as claimed in claim 1, wherein a cutting speed with which the tool is to be moved with regard to the material is in a range from 50 to 150 m/min, wherein a rotational speed of the tool is above 1300 rpm.

10. A method for machining a workpiece, comprising:
   providing a tool with a blade having a cutting angle smaller than 10°;
   rotating the tool in the range between 2650 rpm and 7800 rpm, wherein the tool is characterized by parameters determined as a function of specific cutting force components by means of the equation $$\begin{bmatrix} F_x(\theta) \\ F_y(\theta) \\ F_z(\theta) \end{bmatrix} = J(\theta) \begin{bmatrix} \overline{K}_{ct}(\theta) \\ \overline{K}_{cr}(\theta) \\ \overline{K}_{cz}(\theta) \\ \overline{K}_{et}(\theta) \\ \overline{K}_{er}(\theta) \\ \overline{K}_{ez}(\theta) \end{bmatrix}$$

whereby $\overline{K}_{ct}, \overline{K}_{cr}, \overline{K}_{cz}, \overline{K}_{et}, \overline{K}_{er}, \overline{K}_{ez}$ are mean specific cutting forces.

11. The method as claimed in claim 10, wherein a cutting width is in a range from 0.01 mm to 0.2 mm.

12. The method as claimed in claim 10, wherein a cutting depth is in a range from 0.5 mm to 4 mm.

13. The method as claimed in claim 10, wherein a cutting speed with which the tool is moved with regard to the material is in a range from 50 to 150 m/min.

14. The method as claimed in claim 10, wherein the machined workpiece is selected from the group consisting of a ceramic, a mixed ceramic and a ceramic glass.

15. A method for machining a workpiece, comprising:
providing a tool with a blade having a cutting angle smaller than 10°;
operating the tool dry; and
rotating the tool at a rotational speed above 1300 rpm,
wherein the tool is characterized by parameters determined as a function of specific cutting force components by means of the equation $$\begin{bmatrix} F_x(\theta) \\ F_y(\theta) \\ F_z(\theta) \end{bmatrix} = J(\theta) \begin{bmatrix} \overline{K}_{ct}(\theta) \\ \overline{K}_{cr}(\theta) \\ \overline{K}_{cz}(\theta) \\ \overline{K}_{et}(\theta) \\ \overline{K}_{er}(\theta) \\ \overline{K}_{ez}(\theta) \end{bmatrix}$$

whereby $\overline{K}_{ct}, \overline{K}_{cr}, \overline{K}_{cz}, \overline{K}_{et}, \overline{K}_{er}, \overline{K}_{ez}$ are mean specific cutting forces.

16. The method as claimed in claim 15, wherein a cutting speed is above a heat conduction speed of the workpiece.

17. The method as claimed in claim 15, wherein the blade effects a continual material breakage without cutting the material.

18. The method as claimed in claim 15, wherein a material of the workpiece is selected from the group consisting of granite, marble, concrete, asphalt, brickwork, ceramics, mixed ceramics, and ceramic glasses.

* * * * *